United States Patent [19]

Skurikhin et al.

[11] 4,190,888
[45] Feb. 26, 1980

[54] DIGITAL DEVICE FOR DETERMINING CARBON CONTENT IN IRON-CARBON MELTS

[75] Inventors: Vladimir I. Skurikhin; Leonid S. Fainzilberg; Leonid S. Zhitetsky, all of Kiev, U.S.S.R.

[73] Assignee: Institut Kibernetiki Akademii Nauk Ukrainskoi S S R, Kiev, U.S.S.R.

[21] Appl. No.: 913,908

[22] Filed: Jun. 8, 1978

[30] Foreign Application Priority Data

Jun. 13, 1977 [SU] U.S.S.R. .................. 2496596

[51] Int. Cl.² ............... G06F 15/46; G01N 25/02
[52] U.S. Cl. .............................. 364/497; 73/17 R; 75/60; 364/557
[58] Field of Search ............. 364/497, 499, 500, 496, 364/472, 557, 477; 75/59, 60, 130 R, 132, 133, 129; 73/17R, 341, 359, 360, 361; 324/103 R, 103 P, 104

[56] References Cited

U.S. PATENT DOCUMENTS

| | | | |
|---|---|---|---|
| 3,329,495 | 7/1967 | Ohta et al. | 364/497 X |
| 3,475,599 | 10/1969 | Schwartzenberg et al. | 364/500 X |
| 3,816,720 | 6/1974 | Bauer et al. | 364/500 |
| 3,824,837 | 7/1974 | Nagaoka et al. | 73/17 R |
| 3,891,834 | 6/1975 | Warsinski | 364/497 |
| 4,088,974 | 5/1978 | Zhitetsky et al. | 364/499 X |

Primary Examiner—Joseph F. Ruggiero
Attorney, Agent, or Firm—Haseltine, Lake & Waters

[57] ABSTRACT

The device according to the invention comprises a follow-up analog-to-digital converter having an input whereto there is applied a signal carrying information on the actual temperature of the melt, a conversion suppression input, a synchronized clock pulse output, synchronized code pulse outputs, and a parallel code output; a local temperature increments criminator having inputs connected to the synchronized code pulse outputs of the follow-up analog-to-digital converter, and outputs; a time interval discriminator having reset inputs connected to the outputs of the local temperature increments discriminator, a count input connected to the synchronized clock pulse output of the follow-up analog-to-digital converter, and an output connected to the conversion suppression input of the follow-up analog-to-digital converter; a digital display unit having an information input connected to the parallel code output of the follow-up analog-to-digital converter, and a control input connected to the output of the time interval discriminator.

1 Claim, 1 Drawing Figure

DIGITAL DEVICE FOR DETERMINING CARBON CONTENT IN IRON-CARBON MELTS

FIELD OF THE INVENTION

The present invention relates to computer technology and, in particular, to digital computing devices for determining the carbon content in iron-carbon melts on the basis of temperature arrests in the course of melt cooling.

The invention is applicable to the physiochemical analysis of metals and alloys; it can be used, for example, in ferrous metallurgy for automatically checking the carbon content in molten steel.

BACKGROUND OF THE INVENTION

Known in the art is a digital device for automatically checking the carbon content in metal with reference to temperature arrests on the cooling curve (cf. UK Pat. No. 1,477,564), which comprises an analog-to-digital converter to whose input there is applied a signal carrying information on the actual temperature of the melt. The device also includes a clock pulse generator. Outputs of the analog-to-digital converter are connected, via a synchronization unit for distributing code and clock pulses in time, to add and subtract inputs of a reversible counter, and to inputs of a local temperature increments discriminator. The reversible counter is intended for generating a parallel code of the actual temperature. The local temperature increments discriminator is adjusted so that a pulse is formed at one of its outputs each time a certain positive or negative value $\epsilon_o$ is set therein. An output of the clock pulse generator is connected via the synchronization unit to a count input of a time interval discriminator intended for selecting time intervals during which there occur predetermined temperature increments $\pm\epsilon_o$. Reset inputs of the time interval discriminator are connected to outputs of the local temperature increments discriminator. The time interval discriminator is constructed so that at its output there is formed a signal only when the selected time interval exceeds a predetermined threshold $\tau_o$. The output of the time interval discriminator is connected to a control input of a register and a set intput of a flip-flop. The register is connected with its information input to an information output of the reversible counter, and via a functional code converter to an information input of a digital display unit whose control input is connected to a set output of the flip-flop. The functional code converter is designed for converting a parallel code of the liquidus temperature $T_1$ to a parallel code of carbon content C in the melt, which is found as follows:

$$C = f(T_1), \qquad (1)$$

where f is a general non-linear operator.

The above device operates as follows. From the analog-to-digital converter code pulses are applied via the synchronization unit to the inputs of the local temperature increments discriminator and to the add and subtract inputs of the reversible counter which responds by forming a parallel code of the actual temperature of the melt. Each time the temperature increment is $\pm\epsilon_o$, at the respective output of the local temperature increments discriminator there is formed a pulse which is applied to the reset inputs of the time interval discriminator to whose count input there are fed synchronized clock pulses.

After each resetting, the time interval discriminator resumes time metering by counting synchronized clock pulses. After a certain time $\tau_o$ since the last resetting of the time interval discriminator at an output of the latter there is formed a pulse. This takes place only if no new pulse is fed to the reset inputs of the discriminator during the time $\tau_o$. The pulse formation at the output of the time interval discriminator is indicative of a temperature arrest caused by crystallization of the melt, i.e. a temperature arrest when during a time equal to $\tau_o$ temperature increments do not exceed a predetermined value $\epsilon_o$.

From the output of the time interval discriminator, the pulse is applied to the control input of the register, whereby the content of the reversible counter, which is the liquidus temperature code, is entered into the register and the flip-flop is set. Being fed with a signal from the set output of the flip-flop the digital display unit displays result of the analysis.

The above device is disadvantageous in that the reversible counter may malfunction during the analysis due to all kinds of interference. In such cases, the parallel code of the reversible counter may be considerably distorted. As a result, at the moment of detecting a temperature arrest, the register is fed with a parallel code substantially different from that of the liquidus temperature, and the digital display unit is fed false information on the carbon content in the melt.

In addition, the arrival of code pulses does not depend on the arrival of clock pulses and vice versa. As a result, in the time interval discriminator the synchronized clock pulses are counted even when the code pulses from the converter for converting the melt temperature signal to a numerical pulse code do not arrive for some reason, for example, because of a failure thereof. Such cessation of the arrival of code pulses may cause the same response of the device as in the case of a temperature arrest in the course of melt cooling. In this case, after a time period equal to $\tau_o$ since the cessation of the arrival of code pulses, the parallel code is entered into the register, which is not the code of the melt's liquidus temperature.

It is an object of this invention to provide, on the basis of simplest elements and units of digital computers, a digital device for determining the carbon counter in iron-carbon melts, which would improve the accuracy of the analysis by automatically correcting the parallel code at the output of the analog-to-digital converter in case of malfunctioning thereof, and by using a single source to generate code and clock pulses.

It is another object of the present invention to improve the reliability of such a device.

These and other objects of the invention are attained by providing a digital device for determining the carbon content in iron-carbon melts, comprising an analog-to-digital converter to whose input there is applied a signal carrying information on the actual temperature of the melt, electrically connected to a local temperature increments discriminator whose outputs are connected to reset inputs of a time interval discriminator having also a count input whereto synchronized clock pulses are applied, and an output electrically connected to a control input of a digital display unit to whose information input there is fed a parallel code of the carbon content in the melt, wherein, in accordance with the invention the analog-to-digital converter is a follow-up converter having a synchronized clock pulse output, two synchronized code pulse outputs and conversion suppression input; the electrical connection between the analog-to-digital converter and the local temperature increments discriminator being effected connecting the synchronized code pulse outputs of the follow-up analog-to-digital converter to inputs of the local temperature increments discriminator, the synchronized clock pulse output of the converter being connected to the count input of the time interval discriminator, the conversion suppression input of the converter being connected to an output of the time interval discriminator, a parallel code output of the converter being connected to an information input of a digital display unit.

Such a device improves the accuracy of the analysis.

BRIEF DESCRIPTION OF THE ATTACHED DRAWINGS

Other objects and advantages of the present invention will become more apparent from the following detailed description of a preferred embodiment thereof, taken in conjunction with the accompanying drawing which is a block diagram of a digital device for determining the carbon content in iron-carbon melts according to the invention.

DETAILED DESCRIPTION OF THE INVENTION

Figure 1:
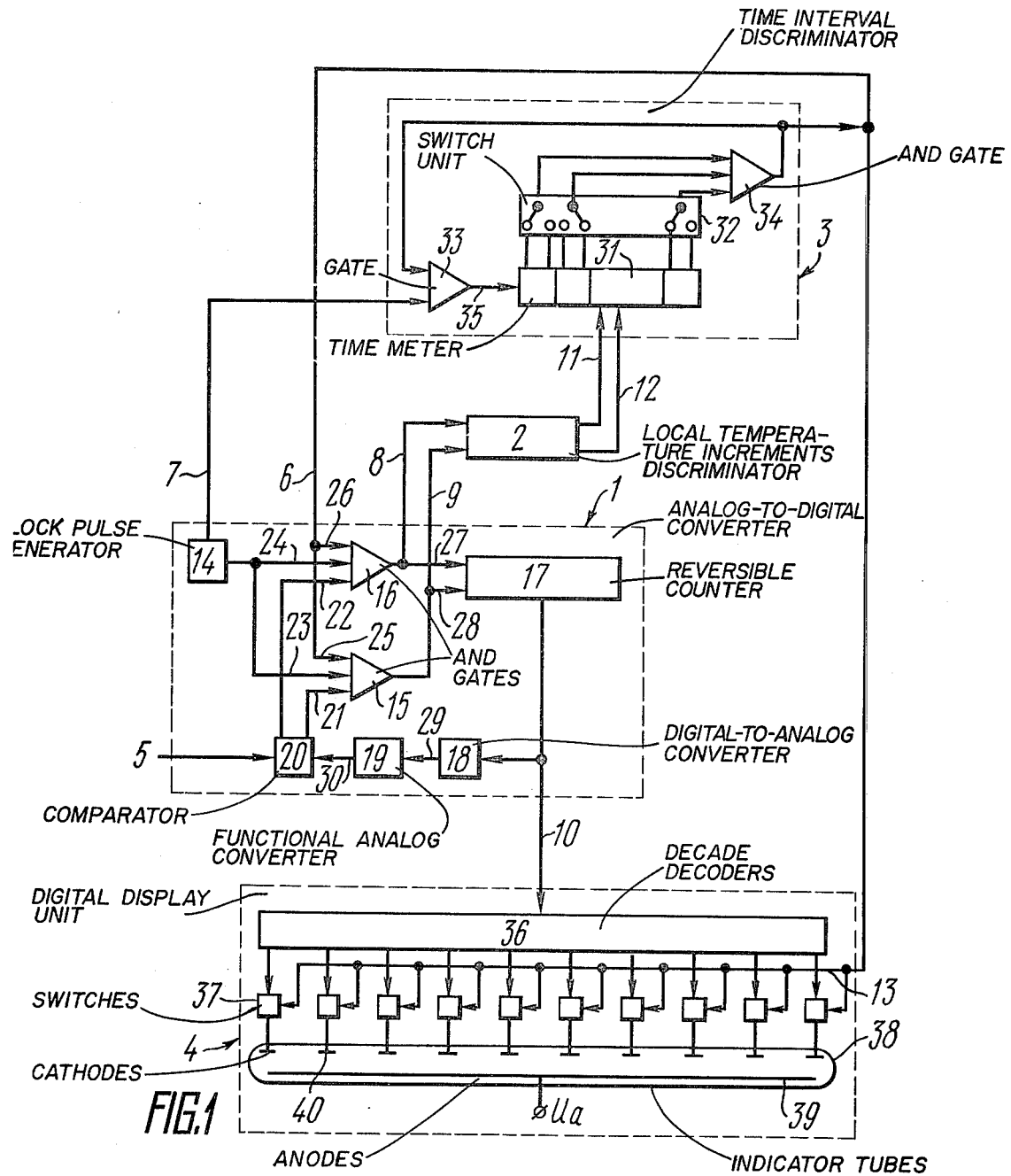

The proposed digital device for determining the carbon content in iron-carbon melts may well be employed in combination with any known measuring device adapted for generating a signal indicative of the actual temperature of the melt in the course of its cooling.

The digital device for determining the carbon content in iron-carbon melts, as shown in the drawing, comprises a follow-up analog-to-digital converter 1, a local temperature increments discriminator 2, a time interval discriminator 3 and a digital display unit 4.

The follow-up analog-to-digital converter 1 has an input 5 whereto there is applied a signal carrying information on the actual temperature of the melt, a conversion suppression input 6, a synchronized clock pulse output 7, and outputs 8, 9 for synchronized code pulses corresponding to positive and negative temperature increments. The converter 1 also has an output 10 for a parallel code, connected to an information input of the digital display unit 4.

The outputs 8 and 9 of the converter 1 are connected to inputs of the discriminator 2. An output 11 of the discriminator 2 for delivering pulses at moments when positive local temperature increments reach a predetermined value $\pm\epsilon_o$, is connected to a first reset input of the discriminator 3. An output 12 of the discriminator 2 for delivering pulses at moments when negative local temperature increments reach a predetermined value $-\epsilon_o$, is connected to a second reset input of the discriminator 3.

A count input of the discriminator 3 is connected to the output 7 of the converter 1, whereas its output is connected to the conversion suppression input 6 of the converter 1, and to a control input of the digital display unit 4.

The converter 1 is intended for converting the actual temperature of liquid metal into a parallel code, and for forming synchronized code and clock pulses.

The converter 1 comprises a clock pulse generator 14, AND gates 15 and 16, a reversible counter 17, a digital-to-analog converter 18, a functional analog converter 19, and a comparator 20.

The generator 14 has an output and an additional output. At the additional output of the generator 14 there are formed pulses shifted in time relative to the pulses formed at the output thereof. The shifting of pulses in time is necessary to prevent malfunctioning of the device. A first input of the comparator 20 is the input 5 of the converter 1.

Each of the AND gates 15 and 16 has three inputs, with an input 21 of the AND gate 15 and an input 22 of the AND gate 16 being connected to respective outputs of the comparator 20. An input 23 of the AND gate 15 and an input 24 of the AND gate 16 are combined and connected to the output of the generator 14 whose other output is the synchronized clock pulse output 7 of the converter 1.

Inputs 25 and 26 of the respective AND gates 15 and 16 are also combined to form the conversion suppression input 6.

An output of the AND gate 16 is connected to an add input 27 of the reversible counter 17 and is the synchronized code pulse output 8. An output of the AND gate 15 is connected to a subtract input 28 of the reversible counter 17 and is the synchronized code pulse output 9.

An information output of the reversible counter 17 connected to an input of the digital-to-analog converter 18 is the parallel code output 10 of the converter 1.

An output 29 of the converter 18 is connected to an input of the converter 19 having an output 30 connected to a second input of the comparator 20.

The functional analog converter 19 is designed for converting analog signals in compliance with the condition $$T_2 = f^{-1}(T_1), \qquad (2)$$

where $T_1$ is a signal at the input of the converter 19, $T_2$ is a signal at the output of the converter 19, $f^{-1}$ is a non-linear operator inverse to the operator f in (1).

The local temperature increments discriminator 2 is adjusted so that a pulse is produced at one of its outputs each time a certain positive or negative number $\epsilon_o$ is set therein. The function of discriminator may be performed by a reversible counter. In this case the add and subtract inputs of the reversible counter are the inputs of the discriminator 2, whereas its add and subtract overflow outputs are the outputs of the discriminator 2.

The time interval discriminator 3 is adapted for selecting time intervals during which predetermined temperature increments occur and is adjusted so that after a certain time since its resetting at its output there is formed a signal if during this time the discriminator 3 is not reset. This discriminator may be a controlled time meter.

According to a preferred embodiment of the discriminator 3 described below, the controlled time meter includes a time meter 31, a switch unit 32, a gate 33 and an AND gate 34.

Set and reset outputs of each digit of the time meter 31 are connected to two poles of a respective switch of the switch unit 32. The central taps of all the switches of the switch unit 32 are connected to inputs of the AND gate 34. By changing the position of switches of the switch unit 32, the inputs of the AND gate 34 can be connected to the set or reset output of the respective digit of the time meter 31. By changing the position of switches of the switch unit 32, the discriminator 3 is adjusted to a predetermined time interval $\tau_o$.

An output of the AND gate 34 is connected to a control input of the gate 33. This output is the information output of the controlled time meter and the output of the discriminator 3.

The input of the gate 33 is the count input of the controlled time meter and the count input of the discriminator 3.

An output 35 of the gate 33 is connected to a count input of the time meter 31 whose reset inputs are the reset inputs of the controlled time meter and the reset inputs of the discriminator 3.

According to the embodiment, under review, the digital display unit 4 comprises decade decoders 36, switches 37 and indicator tubes 38. The drawing conventionally shows the connection of one indicator tube 38.

Inputs of the decoders 36 make up the information input of the digital display unit 4, and are connected to digit outputs of the respective decade of the reversible counter 17.

The inputs of the decoders 36 are connected to inputs of the switches 37. Control inputs of the switches 37 are combined and serve as the control input 13 of the digital display unit 4.

The anodes 39 of the indicator tubes 38 are connected to a source of anode voltage $U_a$. The cathodes of the indicator tubes 38 are constructed as ten digits connected to the outputs of the switches 37.

The digital device for determining the carbon content in iron-carbon melts operates as follows.

An analog signal carrying information on the actual temperature of the liquid metal being analyzed in the process of cooling is fed to the input 5 of the follow-up analog-to-digital converter 1, i.e. to the first input of the comparator 20. To the second input of the comparator 20 from the output 30 of the analog functional converter 19 there is fed a signal $T_2$. Depending on the sign of the difference of these two signals, the pulses generated, by the generator 14 are applied through the AND gates 15, 16 to the add input 27 or to the subtract input 28 of the reversible counter 17, said pulses being synchronized code pulses. In this case, a parallel code generated in the reversible counter 17 is converted by the digital-to-analog converter 18 to the analog signal $T_1$ which is fed to the input of the functional analog converter 19. Thus, in the process of metal cooling there is performed follow-up conversion of the analog signal carrying information on the actual temperature of the liquid metal to a parallel code. This code is functionally related to the actual temperature of the melt by the operator f.

In the course of the follow-up conversion of the actual temperature of the liquid metal to the code, the synchronized code pulses are applied from the outputs 8 and 9 of the converter 1 to the inputs of the local temperature increments discriminator 2, whereas the synchronized clock pulses are applied from the output 7 of the converter 1 to the count input of the discriminator 3 and through the gate 33 to the count input of the time meter 31.

The local temperature increments discriminator 2 operates so that each time a number of pulses fed to its inputs exceeds the value $\epsilon_o$, at its outputs there are formed pulses.

As the temperature of the melt changes in the course of its cooling, the time interval discriminator 3 selects time intervals between the moments of arrival of the pulses from the outputs 11 and 12 of the discriminator 2 at the reset inputs of the time meter 31, the selection of time intervals being done by counting synchronized clock pulses fed to the count input of the time meter 31 since the last resetting thereof.

If the time interval does not exceed a predetermined initial threshold $\tau_o$ set with the aid of the switch unit 32, no signal is formed at the output of the AND gate 34. Thus, if the rate of cooling is so high that the predetermined temperature increments $\epsilon_o$ occur within the time period not exceeding $\tau_o$, no signal is formed at the output of the AND gate 34.

When there appears a temperature arrest caused by crystallization of the metal, no signals are formed at the outputs 11 and 12 of the discriminator 2. In this case after a time $\tau_o$ since the last resetting of the time counter 31 there is formed a signal at the output of the AND gate 34, which is applied to the control input of the gate 33 and to the inputs 25 and 26 of the AND gates 15 and 16 whereby the feeding of synchronized clock pulses of the counter 31 and of synchronized code pulses to the reversible counter 17 is discontinued, with the follow-up conversion of the signal carrying information on the actual temperature of the melt to a parallel code being discontinued till the end of the analysis. Simultaneously, from the output of the AND gate 34 a signal is applied to the control inputs of the switches 37, the control inputs being the control inputs 13 of the digital display unit 4. As a result, the feed circuit of the indicator tubes 38 is closed and the tubes 38 are switched on for digital display of the content of the reversible counter 17.

Insofar as the follow-up conversion of the signal carrying information on the actual temperature of the melt to a parallel code stops in case of a temperature arrest when the melt temperature has reached the liquidus temperature, the content of the reversible counter 17, entered in the digital display unit 4, supplies information on the carbon content C in the melt in compliance with the relation (1).

It follows from the above that the follow-up conversion of the signal carrying information on the actual temperature of the melt to a parallel code allows the parallel code to be automatically corrected at the output of the analog-to-digital converter in case of malfunctions of the reversible counter 17.

If such malfunctioning occurs in the presence of a temperature arrest, the synchronized code pulses are applied to the inputs of the local temperature increments discriminator until the parallel code is corrected, which prevents transmission of false information to the digital display unit.

The employment in the device of a single source for forming synchronized code and clock pulses prevents misoperation of the device when no temperature arrest occurs during cooling of the melt, which also rules out transmission of false information to the digital display unit.

The use of simplest computer elements and units in the device ensures a high reliability, low cost and small dimensions thereof. The device can operate without any maintenance over long periods of time.

Taken in combination with any conventional measuring device adapted for forming a signal containing information on the actual temperature of a melt in the course of its cooling, the proposed device may perform the function of a digital carbon content transducer in a closed-loop control system for controlling steel smelting processes with the use of a computer.

What is claimed is:

1. A digital device for determining the carbon content in iron-carbon melts, comprising: a follow-up analog-to-digital converter, having an input with an applied signal carrying information on the actual temperature of the melt, a conversion suppression input, an synchronized clock pulse output, first and second synchronized code pulse outputs, a parallel code output, said follow-up analog-to-digital converter converting only up to a moment of temperature hold caused by crystallization of the melt; a local temperature increments discriminator, having a first input and a second input connected to said respective first and second synchronized code pulse outputs of said follow-up analog-to-digital converter, a first output and a second output of said local temperature increments discriminator; a time interval discriminator, having reset inputs connected to said first and second outputs of said local temperature increments discriminator, a count input connected to said synchronized clock pulse output of said follow-up analog-to-digital converter, an output connected to said conversion suppresion input of said follow-up analog-to-digital converter; a digital display unit, having an information input connected to said parallel code output of said follow-up analog-to-digital converter, a control input connected to said output of said time interval discriminator.

* * * * *